(12) United States Patent
Letinois et al.

(10) Patent No.: US 10,047,065 B2
(45) Date of Patent: Aug. 14, 2018

(54) FORMATION OF CHROMANES BASED ON INTERMOLECULAR REACTION OF ALKYNES WITH DIMETHYLFURAN IN THE PRESENCE OF GOLD(I) COMPLEXES

(71) Applicant: DSM IP ASSETS B.V., Heerlen (NL)

(72) Inventors: Ulla Letinois, Kaiseraugst (CH);
Thomas Netscher, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/535,477

(22) PCT Filed: Dec. 9, 2015

(86) PCT No.: PCT/EP2015/079111
§ 371 (c)(1),
(2) Date: Jun. 13, 2017

(87) PCT Pub. No.: WO2016/096566
PCT Pub. Date: Jun. 23, 2016

(65) Prior Publication Data
US 2017/0349563 A1    Dec. 7, 2017

(30) Foreign Application Priority Data
Dec. 17, 2014    (EP) .................................... 14198491

(51) Int. Cl.
| | |
|---|---|
| *C07D 311/04* | (2006.01) |
| *C07C 1/32* | (2006.01) |
| *C07F 7/08* | (2006.01) |
| *C07C 45/00* | (2006.01) |
| *C07C 37/14* | (2006.01) |
| *C07C 37/00* | (2006.01) |

(52) U.S. Cl.
CPC ............ *C07D 311/04* (2013.01); *C07C 1/321* (2013.01); *C07C 37/00* (2013.01); *C07C 37/14* (2013.01); *C07C 45/00* (2013.01); *C07F 7/0809* (2013.01)

(58) Field of Classification Search
CPC ....... C07D 311/04; C07C 1/321; C07C 45/00; C07C 37/14; C07C 37/00; C07F 7/0809
See application file for complete search history.

(56) References Cited

FOREIGN PATENT DOCUMENTS

WO    WO-2013016531 A2 *    1/2013    ........... C07D 249/06

OTHER PUBLICATIONS

Krafft, M. E., "Addition of Hexacarbonyldicobalt-Stabilized Propargyl Cations to Alkenes." The Journal of organic chemistry 61.11 (1996): 3912-3915.*
Murakami, T., "Efficient stereocontrolled synthesis of sphingadienine derivatives." Tetrahedron 61.39 (2005): 9233-9241.*
International Search Report for PCT/EP2015/079111, dated Apr. 25, 2016, 4 pages.
Written Opinion of the ISA for PCT/EP2015/079111, dated Apr. 25, 2016, 7 pages.
Huguet et al. "Intermolecular Gold (I)—Catalyzed Cyclization of Furans with Alkynes Formation of Phenols and Indenes", Chemistry, URL:http://onlinelibrary.wiley.com/doi/10.1002/chem.201300646/pdf, vol. 19, No. 21, pp. 6581-6585, (May 2013).
Uto et al. "Design, ex vivo synthesis and biological activities of plant constituents containing an isoprene side chain based on isoprenomics", Bulletin of Institute of Technology and Science the University of Tokushima, URL:http://www.tokushim-u.ac.jp/files/00033497/bulletin2008.pdf, pp. 52-56, (Jan. 2008).
Lee et al. "Enantioselective Total Synthesis of Eunicenone A", Journal of the American Chemical Society, vol. 123, No. 9, pp. 1872-1877, (Mar. 2001).

* cited by examiner

*Primary Examiner* — John M Mauro
(74) *Attorney, Agent, or Firm* — Nixon & Vanderhye P.C.

(57) ABSTRACT

The present invention relates to a method of preparing chromanes from 2,5-dimethylfuran and substituted alkynes comprising an long chain unsaturated alkyl group as substituent in the alpha position of a substituted phenol followed by oxidation, reduction and acid ring closure. It is particularly advantageous to use 2,5-dimethylfuran as this offers an ecological beneficial synthesis of β-tocopherol.

13 Claims, No Drawings

FORMATION OF CHROMANES BASED ON INTERMOLECULAR REACTION OF ALKYNES WITH DIMETHYLFURAN IN THE PRESENCE OF GOLD(I) COMPLEXES

This application is the U.S. national phase of International Application No. PCT/EP2015/079111 filed Dec. 9, 2015 which designated the U.S. and claims priority to EP Patent Application No. 14198491.4 filed Dec. 17, 2014, the entire contents of each of which are hereby incorporated by reference.

TECHNICAL FIELD

The present invention relates to the field of the formation phenol derivatives and particularly to the field of synthesis of tocopherol and tocotrienol.

BACKGROUND OF THE INVENTION

An important class of the chromane compounds are vitamin E and its esters. Due to the high relevance of this substance class in food and feed industry, new synthetic pathways of tocopherols and tocotrienols are of high interest.

J. Am. Chem. Soc. 2000, 122, 11553-11554 discloses that the gold(III) salt $AuCl_3$ catalysis an intramolecular ring closure reaction of ω-alkynylfuran.

A. S. K. Hashmi et al., Adv. Synth. Catal. 2006, 348, 709-713 disclosed the first intermolecular reaction of an alkyne with furan using binuclear gold(l) complexes. However, said reaction formed next to a substituted phenol an almost equimolar amount of an alkenylfuran as side product.

N. Huguet et al. disclosed in Chem. Eur. J. 2013, 19, 6581-6585 an intermolecular gold(I) catalysed cyclization of furans with alkynes. Next to aromatic substituted alkynes such as phenylacetylene only very short chain alkyl acetylenes have been used.

Y. Román-Leshkov et al., Nature 2007, 447, 982-985, discloses that 2,5-dimethylfuran can be obtained from biomass.

SUMMARY OF THE INVENTION

The present invention offers a new synthetic pathway for chromane synthesis, particularly for tocopherols and tocotrienols.

In a first aspect the present invention relates to a process according to claim 1 to the formation of specific phenols (formula I) being substituted in the ortho position to the phenolic OH groups with a long hydrocarbonyl chain having a double bond in a specific position allowing to be used of said product as intermediate for the synthesis of chromanes.

This pathway offers a possibility for the synthesis of chromanes in a high yield and selectivity. Using 2,5-dimethylfuran enables the synthesis of chromanes from biomass. Hence, a synthesis of chromanes with a good ecological food print is possible. Particularly important is the synthesis of β-tocophenol and β-tocotrienol by this advantageous process. As α-tocopherol, resp. α-tocotrienol, can be prepared by methylation from β-tocophenol, resp. β-tocotrienol. This process offers also a very interesting synthetic route for α-tocopherol and α-tocotrienol.

This process is very advantageous as any Friedel-Crafts alkylation using substoichiometric Lewis-acidic salts becomes redundant and corrosive conditions can be avoided.

Further aspects of the invention are subject of further independent claims. Particularly preferred embodiments are subject of dependent claims.

DETAILED DESCRIPTION OF THE INVENTION

In a first aspect the present invention relates to a process of preparing a compound of formula (I)

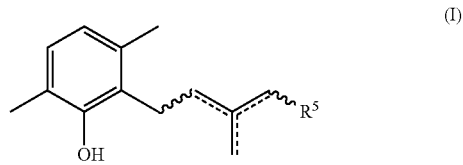

comprising the step of reacting compound of formula (II) with formula (III)

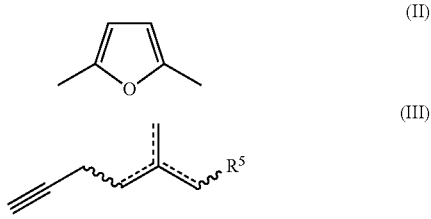

wherein $R^5$ represents either a completely saturated $C_{5-25}$-alkyl group or a $C_{5-25}$-alkyl group comprising at least one carbon-carbon double bond;

wherein the dotted line indicates a double bond which is localized in one of the three indicated positions;

and wherein the wavy line represents a carbon-carbon bond which when linked to the carbon-carbon double bond is either in the Z or in the E-configuration;

in the presence of a gold(I) complex.

The term "independently from each other" in this document means, in the context of substituents, moieties, or groups, that identically designated substituents, moieties, or groups can occur simultaneously with a different meaning in the same molecule.

The term "vitamin E" is used in the present document as a generic descriptor for all tocol and tocotrienol derivatives exhibiting qualitatively the biological activity of α-tocopherol (IUPAC-IUB Recommendation 1981, Eur. J. Biochem. 123, 473-475 (1982)).

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —$CH(CH_3)$—$CH_2$—$CH_3$ is considered as a $C_4$-alkyl group.

The term "hydrogen" means in the present document H and not $H_2$.

In the present document any single dotted line represents the bond by which a substituent is bound to the rest of a molecule.

The chirality of an individual chiral carbon centre is indicated by the label R or S according to the rules defined by R. S. Cahn, C. K. Ingold and V. Prelog. This R/S-concept and rules for the determination of the absolute configuration in stereochemistry is known to the person skilled in the art.

In case identical labels for symbols or groups are present in several formulae, in the present document, the definition of said group or symbol made in the context of one specific formula applies also to other formulae which comprises said same label.

The expression "process of preparation" is a synonym for "method of preparation" and can be used interchangeable to each other.

The anion tetra(3,5-bis(trifluoromethyl)phenyl)borate is abbreviated in the present document as "BAr$_F^-$" being known to the person skilled in the art also by the abbreviation "[BAr$^F_4$]$^-$".

In the present document a specific structural element is used in some formulae. The use of said specific structural element is clarified by the following generic formula (X).

(X)

In formula (X) the dotted line indicates a double bond which is localized in one of the three indicated positions and the wavy line represents a carbon-carbon bond which when linked to the carbon-carbon double bond is either in the Z or in the E-configuration. A and B are residues attached to said structural element of the molecule.

Thus formula (X) actually represents the 5 different possibilities, i.e. (X-a), (X-b), (X-c), (X-d) or (X-e), by one formula.

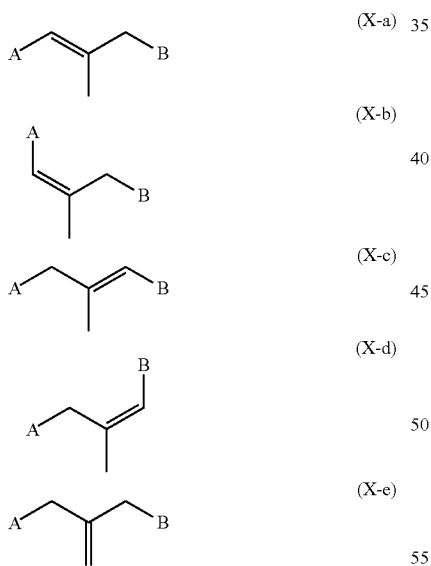

(X-a)

(X-b)

(X-c)

(X-d)

(X-e)

Hence, a formula of compound of formula (III) represents the formulae (III-a), (III-b), (III-c), (III-d) or (III-e) by one formula.

(III)

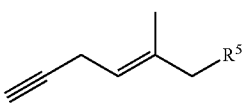

(III-a)

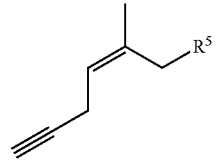

(III-b)

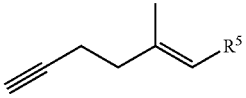

(III-c)

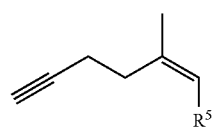

(III-d)

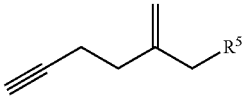

(III-e)

The same concept is to be applied for compounds which comprise said structural element, such as for compounds of formula (I), (I-A), (III), (III'), (III-A), (III-B), (VI) and (VII).

Said process of preparing compound of formula (I) comprises the step of reacting compound of formula (II) with formula (III).

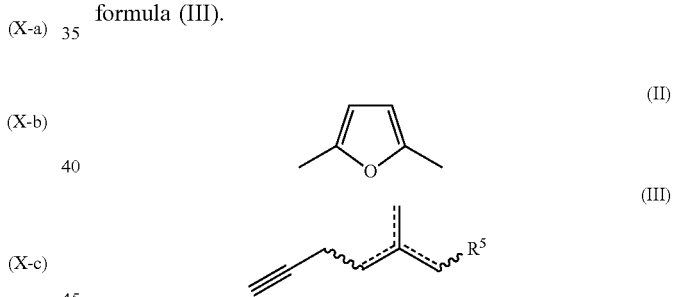

(II)

(III)

Compound of formula (II) is 2,5-dimethylfuran which is commercially available.

Compound of formula (II) can be obtained from biomass such as cellulose. As biomass is a renewable raw material, the use of 2,5-dimethylfuran is very interesting from an ecological and sustainability point of view. The process of obtaining 2,5-dimethylfuran from biomass, respectively from fructose, is described in detail by Y. Román-Leshkov et al., *Nature* 2007, 447, 982-985, the entire content of which is hereby incorporated by reference. Fructose is obtainable from glucose, a building block in cellulose.

The compounds of formula (III) can be produced by the reaction of compound of formula (XIII-a) and from compound of formula (XIII-b)

(XIII-a)

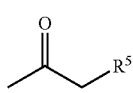
(XIII-b)

wherein X represents a halogen atom, particularly Br, and wherein $R^0$ represents either H or $SiR'_3$ wherein R' represents independently from each other a linear or branched $C_{2-8}$-alkyl group or a $C_{6-12}$-aryl group. Particularly, $R^0$ is $Si(CH_3)_3$ or $Si(CH_2CH_3)_3$ (=$Si(Et)_3$) Or $Si(CH(CH_3)_2)_3$ (=$Si(iPr)_3$) or $Si(C_6H_5)_3$(=$Si(ph)_3$) or $SiCH_3(C_6H_5)_2$ or $Si(CH_3)_2C_6H_5$ or $Si(CH_3)_2(C(CH_3)_3)$.

More particularly, compounds of formula (III) can be obtained from the compounds of formula (XIII-a) and from compound of formula (XIII-b) by the following reaction scheme:

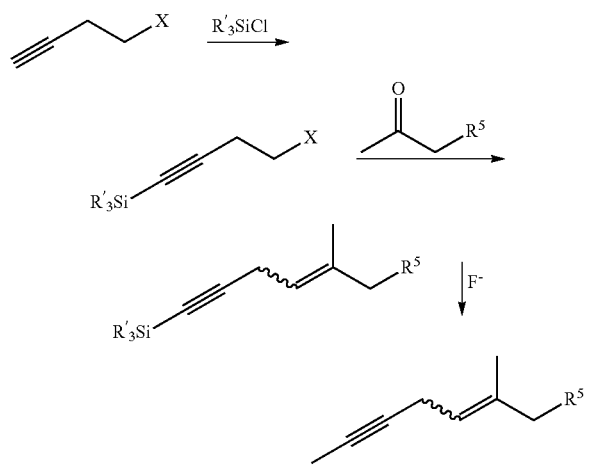

Furthermore, compound of formula (III) can be obtained from the compounds of formula (XIII-c) and from compound of formula (XIII-d) by the following reaction scheme:

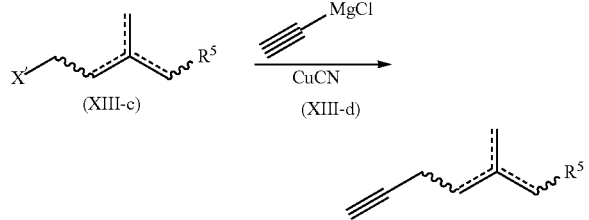

wherein X' represents OH, Cl or Br.

Furthermore, compound of formula (III) can be prepared from compound of formula (XIII-e) by elimination of water.

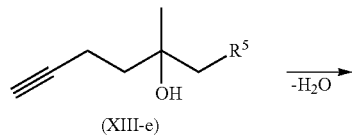

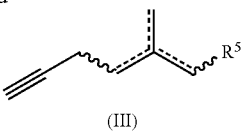
(III)

The compounds of formula

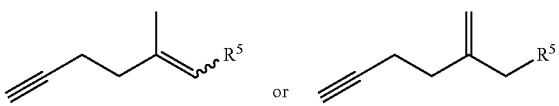

can be produced from compounds of formula

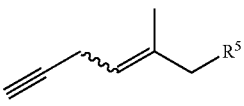

by thermal treatment.

The group $R^5$ in the precedent formulae is particularly either a completely saturated $C_{5-25}$-alkyl group (=$R^{5'}$) or a $C_{5-25}$-alkyl group comprising at least one carbon-carbon double bond.

Particularly $R^5$ is of formula (IV)

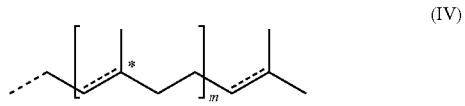

wherein m represents an integer being 0 or 1 or 2 or 3 or 4;

and the dotted line represents the bond by which the substituent of formula (IV) is bound to the rest of the molecule such as of compound of formula (I) or formula (III);

and wherein the double bonds having dotted lines ( ------ ) represent independently from each other either a single carbon-carbon bond or a double carbon-carbon bond;

and wherein * indicates a chiral centre in case the respective double bond having dotted line ( ------ ) represents a single carbon-carbon bond.

Any carbon-carbon double bonds being eventually present in $R^5$ can be in the Z or in the E-configuration. Preferably, they are in the E-configuration, more preferably they are all in the E-configuration in case more than one carbon-carbon double bonds are present in $R^5$.

The chiral centre indicated by * has preferably the R configuration.

In one embodiment, $R^5$ is preferably of formula (IV-A), particularly (IV-ARR), or (IV-B).

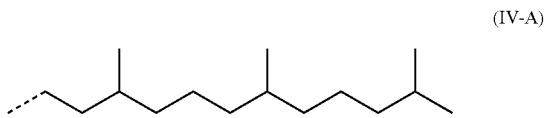

-continued

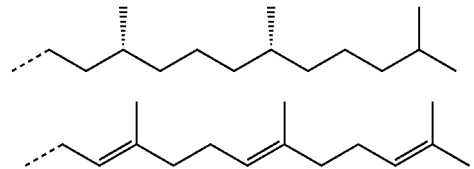
(IV-ARR)

(IV-B)

R⁵, preferably R⁵', is most preferably of formula (IV-A) or (IV-ARR).

Said process of preparing a compound of formula (I) comprises the step of reacting compound of formula (II) with formula (III) in the presence of a gold(I) complex.

The gold(I) complex has preferably the formula [Au(I)OL]AN wherein OL represents an organic ligand and AN represents a single charged anion.

The gold(I) complex has preferably a single charged anion (AN) which is selected from the group consisting of $[BX_4]^-$, $[PX_6]^-$, $[SbF_6]^-$, $[ClO_4]^-$, $CF_3COO^-$, sulfonates, particularly a sulfonate of formula (AN-II), tetra(3,5-bis(trifluoromethyl)-phenyl)borate ($BAr_F^-$), tetraphenylborate, and anions of formula (AN-1)

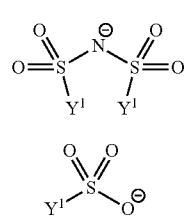
(AN-I)

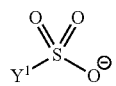
(AN-II)

wherein X represents a halogen atom, particularly F or Cl; and $Y^1$ represents a phenyl or a $C_{1-8}$-alkyl group which preferably is substituted by at least one halogen atom.

Preferably $Y^1$ represents a $CF_3$ group. So, preferably, the anions of formula (AN-I) is the anion of formula (AN-Ia), i.e. the anion of bis(trifluoromethane)sulfonimide, which is also known as triflimidic acid.

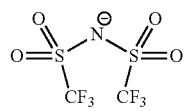
(AN-Ia)

Preferred sulfonates are halogenated anions of organic sulfonic acids, particularly of trifluoromethanesulfonic acid, which is also known as triflic acid. Therefore, the preferred sulfonates are trifluoromethanesulfonates, which are also known as triflates.

In a more preferred embodiment the anion (AN) in step b) is an anion which is selected from the group consisting of $[BX_4]^-$, triflate, and anions of formula (AN-I).

It is preferred that the gold(I) complex has an organic ligand (OL) which is either
- at least one phosphorous containing ligand, particularly a phosphorous containing ligand which is selected from the group consisting of formula (P1), (P2), (P3), (P4), (P5), (P6), (P7) and (P8);

or
- at least an imidazole-2-ylidene ligand, particularly 1,3-bis(2,6-diisopropylphenyl)-1,3-dihydro-2H-imidazol-2-ylidene (=compound of formula (IM));

or
- at least an 1H-1,2,3-triazol ligand, particularly of formula (TR-1) or (TR-2) or (TR-3), more particularly of formula (TR-3);

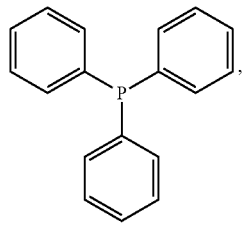
(P1)

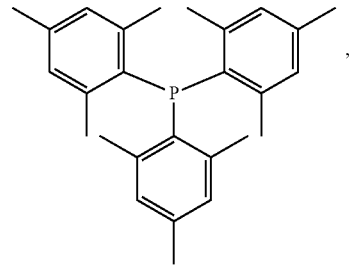
(P2)

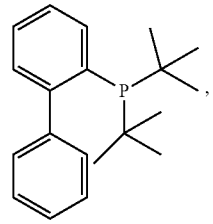
(P3)

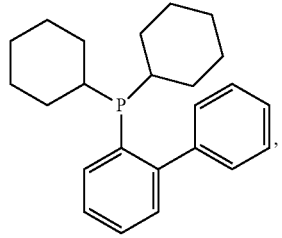
(P4)

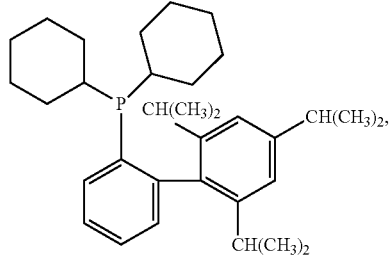
(P5)

-continued

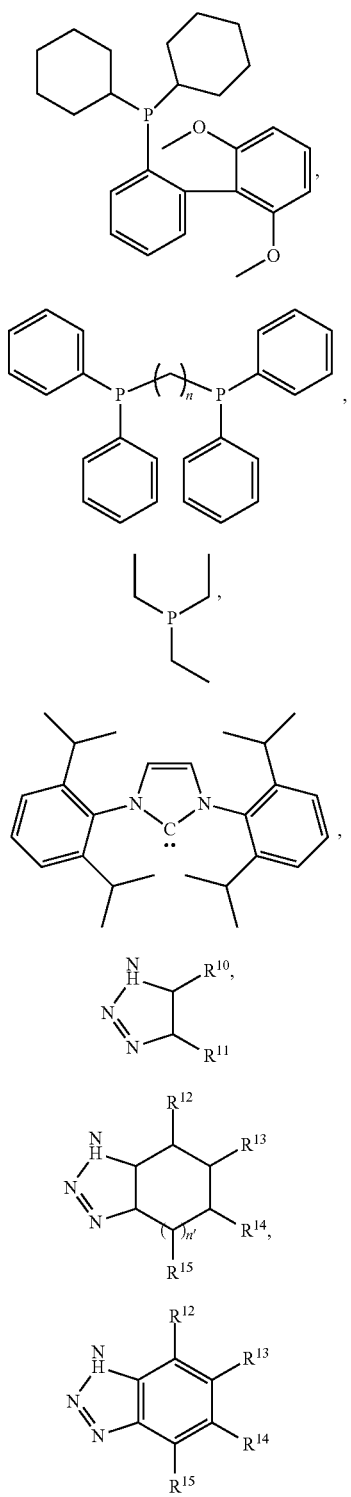

(P6)

(P7)

(P8)

(IM)

(TR-1)

(TR-2)

(TR-3)

wherein $R^{10}$ and $R^{11}$ represent independently from each other either H or a linear or branched $C_{1-10}$-alkyl or $C_{4-10}$-cycloalkyl group; and
wherein $R^{12}$, $R^{13}$, $R^{14}$ and $R^{15}$ represent independently from each other H or a linear or branched $C_{1-6}$-alkyl group;

n stands for an integer of 1-6 and n' stands for 0 or 1 or 2.

The organic ligand (OL) of formula (P4) is also known as CyJohnPhos.

The Au(I) complex can be added to one or a mixture of the starting material of compound of formula (II) and/or formula (III) as such, i.e. particularly in the form of a gold(I) complex of formula [Au(I)OL]AN, or the Au(I)-complex is formed in situ in one of the starting material or the reaction mixture (before or after the reaction has started).

The gold(I) complex is preferably formed in situ in the reaction mixture.

Particularly, the gold(I) complex is prepared from a gold(I) chloro complex and a silver(I) salt. The silver(I) salt is preferably Ag(I)AN. The organic ligand is in this case either present in the reaction of the gold(I) chloro complex with the silver(I) salt or is part of the gold(I) complex. By this reaction the desired gold(I), i.e. preferably [Au(I)OL]AN, is prepared. AgCl formed by this reaction as precipitate does not interfere negatively with the reaction of preparing the compound of formula (I).

Hence, the gold (I) complex is preferably of formula [Au(I)OL]AN wherein OL represents an organic ligand and AN represents a single charged anion and the gold (I) complex is prepared by the reaction of Au(I)OLCl and AgAN.

Preferred Au(I) complexes of the formula [Au(I)OL]AN are selected from the group consisting of

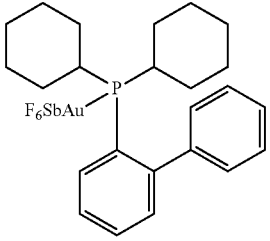

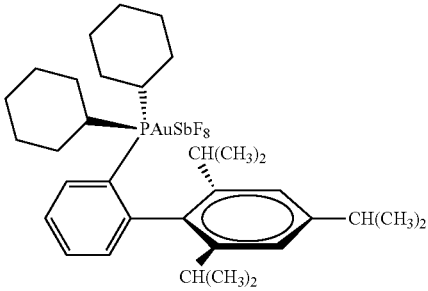

and [Au(I)P6]AN-Ia, wherein P6 is the organic ligand of formula (P6) and AN-Ia is the anion of formula (AN-Ia).

The gold(I) complex is used typically in a molar ratio of gold(I) complex to compound of formula (II) of 1:2 to 1:10,000, particularly 1:10 to 1:3,000, preferably 1:25 to 1:3,000.

The molar ratio of compound of formula (II) to compound of formula (III) is preferably between 0.8 and 1.2, preferably between 0.9 and 1.1, more preferably 1.

The reaction is preferably carried out under normal pressure (i.e. 1013 mbar). The reaction temperature is particularly between 10-50° C., preferably between 15-30° C.

The reaction is usually carried out in an inert solvent (or mixture of inertsolvents). Preferably the solvent (or the mixture of solvents) has a pH of 7 or less than 7. Preferred solvents are halogenated solvents, particularly dichloromethane, 1,2-dichloroethane, chloroform or 2,2,2-trifluoroethanol; or toluene, ethyl acetate, cyclohexanone or acetone. More preferred, the solvents are dichloromethane and 1,2-dichloroethane as well as a mixture of dichloromethane with 5% by volume of 2,2,2-trifluoroethanol.

The reaction of compound of formula (II) with formula (III) yields compound of formula (I).

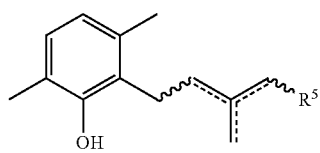

The substituent $R^5$ corresponds to the one used in its starting products, i.e. in formula (II) and (III).

It may be needed that undesired by-products are to be separated. Such separation can be easily performed by standard separation techniques such as distillation or chromatography.

The desired product of formula (I) is formed in very high yield.

Most preferably compound of formula (I) is compound of formula (I-A)

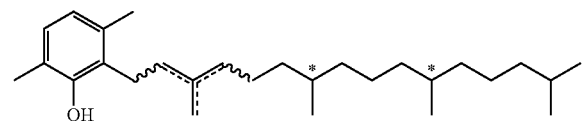

wherein * indicates a chiral centre.

Compound of formula(I) can be further reacted to compound of formula (V). Hence, in a further aspect, the invention relates to a process of preparing a compound of formula (V).

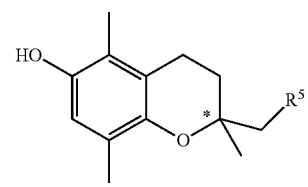

comprising the steps of
a) oxidizing compound of formula (I) to compound of formula (VI)

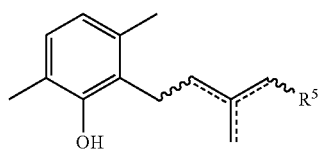

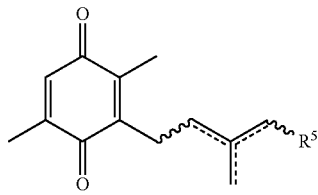

followed by
b) reducing compound of formula (VI) to compound of formula (VII)
followed by

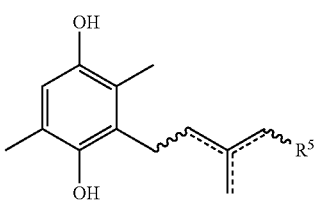

c) acid ring closure of compound of formula (VII) to yield compound of formula (V).

The residue $R^5$ is the same as already discussed for compound of formula (I) resp. (II) and (III).

In step a) compound of formula (I) is oxidized to compound of formula (VI). The oxidation is preferably carried out with air using salcomine as catalyst in ethanol according to the procedure published by A. Stocker, W.-D. Woggon, A. Riuttimann, *Helv. Chim. Acta* 1993, 76, 1729-1738, the entire content of which is hereby incorporated by reference.

In step b) compound of formula (VI) is reduced to compound of formula (VII). The reduction is preferably achieved with sodium dithionite in water according to the method as disclosed by K. Sato, Y. Fujima, A. Yamada *Bull. Chem. Soc. Jap.* 1968, 41, 442-444, the entire content of which is hereby incorporated by reference.

Finally, in step c) compound of formula (V) is formed from compound of formula (VII) by acid ring closure.

Details for step c) are disclosed in WO 2004/046126 A1, the entire content of which is hereby incorporated by reference. Preferred as acids for the ring closure are sulfonic acids, particularly fluorosulphonic acid, methanesulfonic acid, ethanesulphonic acid, trifluoromethanesulphonic acid or benzene- or p-toluenesulphonic acid, respectively. Trifluoromethanesulphonic acid and p-toluenesulphonic acid are the most preferred acid. The amount of acid used for the acid ring closure is preferably 0.01-10 mol-% in relation to compound of formula (VII). The temperature of the ring closure reaction is typically between 20 and 160° C., preferably between 80 and 140° C.

For the present invention, it is important to realize, that all compounds of formula (VII-a), (VII-b), (VII-c), (VII-d) or (VII-e), respectively (covered all by formula (VII)) all yield only one product, i.e. compound of formula (V).

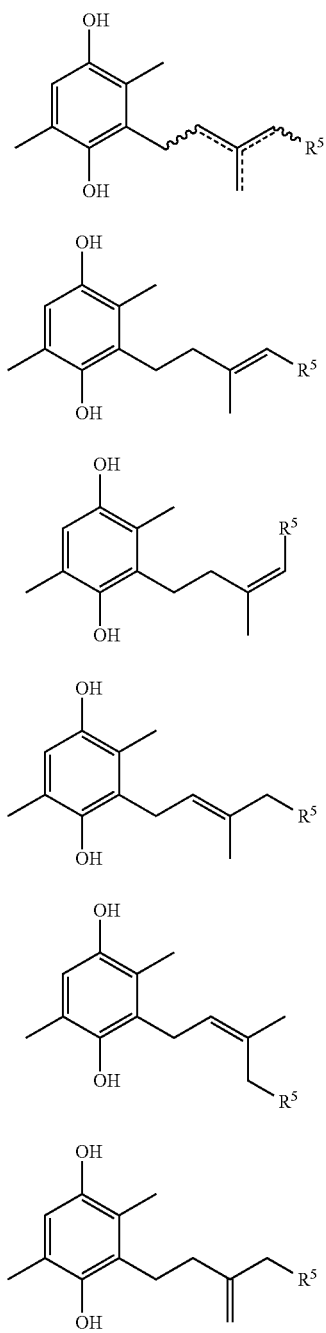

(VII)

(VII-a)

(VII-b)

(VII-c)

(VII-d)

(VII-e)

Hence, a separation of these isomers, or the separation of the isomers of their precursors of formula (I) resp. (VI) resp. (III) is not necessary. This leads to that the overall yield for the complete synthesis of compound of formula (V) from the starting compounds of formula (II) and (III) is very high.

When compound of formula (III) having the formula (IV-B) as substituent $R^5$ is used β-tocotrienol is obtained as compound of formula (V).

When compound of formula (III) having the formula (IV-A) as substituent $R^5$ is used β-tocopherol is obtained as compound of formula (V); It is preferred that by this process compound of formula (V-A) is formed.

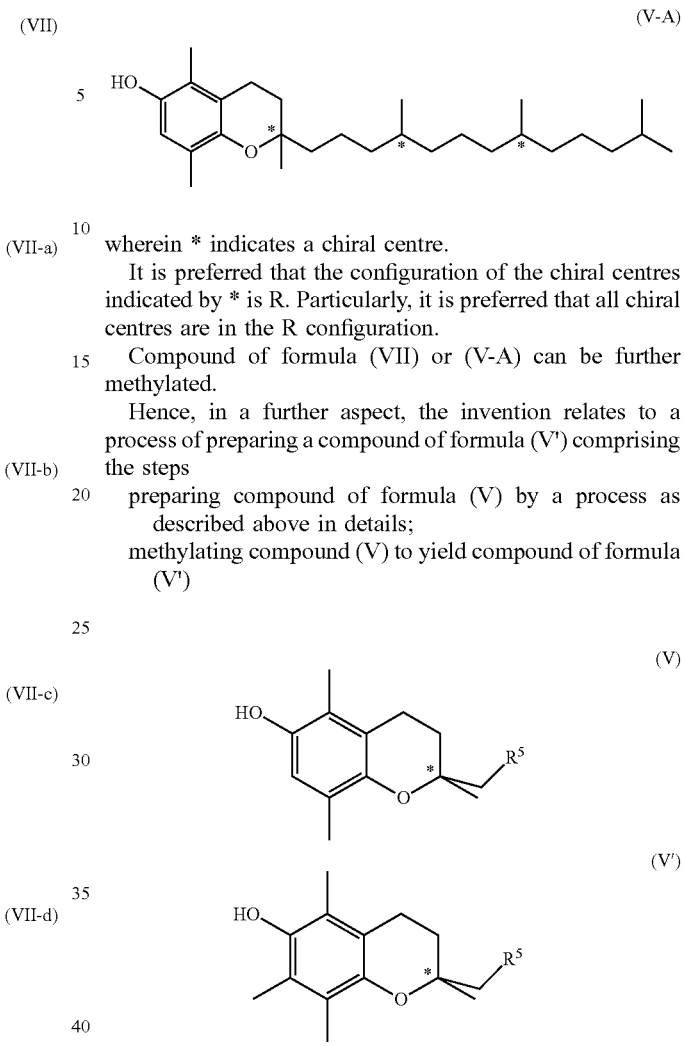

(V-A)

wherein * indicates a chiral centre.

It is preferred that the configuration of the chiral centres indicated by * is R. Particularly, it is preferred that all chiral centres are in the R configuration.

Compound of formula (VII) or (V-A) can be further methylated.

Hence, in a further aspect, the invention relates to a process of preparing a compound of formula (V') comprising the steps preparing compound of formula (V) by a process as described above in details;

methylating compound (V) to yield compound of formula (V')

(V)

(V')

wherein $R^5$ represents either a completely saturated $C_{5-25}$-alkyl group or a $C_{5-25}$-alkyl group comprising at least one carbon-carbon double bond;

and * represents the chiral centre of the chiral isomer.

Said alkylation, by which an H attached to an aromatic ring is replaced by a methyl group attached to an aromatic ring, is known to the person skilled in the art for example from EP 0 769 497 A1 or EP 0 735 033 A1 or Eur. J. Org. Chem., 2007, 1176-1183, the entire content of which is hereby incorporated by reference. Hence, compound of formula (V) is preferably hydroxymethylated or aminomethylated or chloromethylated. The hydroxymethylation or aminomethylation or chloromethylation, respectively, of formula (V) introduces by the use of a formaldehyde or source of formaldehyde such as para-formaldehyde, and HCl, water or methanol or a secondary amine ($HNR''_2$), respectively, $CH_2OH$ or $CH_2Cl$ or $CH_2NR''_2$ (R" represents a $C_{1-8}$-alkyl group or the two R" groups form together a divalent group such as a $C_{4-12}$-alkylene group or $CH_2CH_2$—O—$CH_2CH_2$) group(s), respectively, attached to the aromatic rings. After catalytic hydrogenation said $CH_2OH$ or $CH_2Cl$ or $CH_2NR''_2$ group(s), are transformed to methyl groups, by which compound of formula (V') is obtained.

A further method of methylation is disclosed in U.S. Pat. No. 5,932,748, the entire content of which is hereby incorporated by reference. By this method using a mixed oxide hydrotalcite catalyst a permethylation (all protons attached directly to the aromatic rings are transformed to methyl groups) is obtained.

Therefore, in a preferred embodiment β-tocopherol is transformed to α-tocopherol.

Furthermore, the phenolic group of compound of formula (V) or (V') can be protected by reaction with a protecting agent to form compound of formula (V-P) or (V'-P)

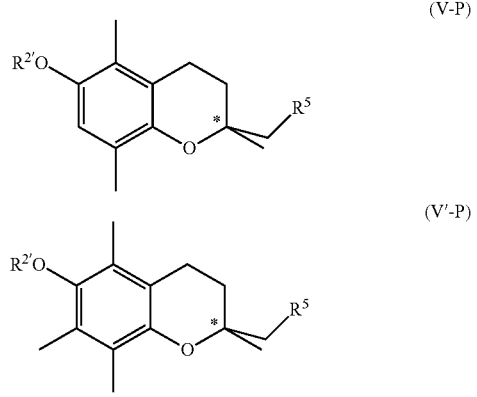

Wherein $R^{2'}$ represents a phenol protecting group which is linked to the oxygen atom which is directly linked to the aromatic ring.

A phenol protection group is a group which protects the phenolic group and can be deprotected easily, i.e. by state-of-the-art methods, to the phenolic group again.

The phenol protection group forms with the rest of the molecule a chemical functionality which is particularly selected from the group consisting of ester, ether or acetal. The protection group can be easily removed by standard methods known to the person skilled in the art.

In case where the phenol protection group forms with the rest of the molecule an ether, the substituent $R^{2'}$ is particularly a linear or branched $C_{1-10}$-alkyl or cycloalkyl or aralkyl group. Preferably the substituent $R^{2'}$ is a benzyl group or a substituted benzyl group, particularly preferred a benzyl group.

In case where the phenol protection group forms with the rest of the molecule an ester, the ester is an ester of an organic or inorganic acid.

If the ester is an ester of an organic acid, the organic acid can be a monocarboxylic acid or a polycarboxylic acid, i.e. an acid having two or more COOH-groups. Polycarboxylic acid are preferably malonic acid, succinic acid, glutaric acid, adipic acid, maleic acid or fumaric acid.

Preferably the organic acid is a monocarboxylic acid.

Hence, the substituent $R^{2'}$ is preferably an acyl group. The acyl group is particularly a $C_{1-7}$-acyl, preferably acetyl, trifluoroacetyl, propionyl or benzoyl group, or a substituted benzoyl group.

If the ester is an ester of an inorganic acid, the inorganic acid is preferably nitric acid or a polyprotic acid, i.e. an acid able to donate more than one proton per acid molecule, particularly selected from the group consisting of phosphoric acid, pyrophosphoric acid, phosphorous acid, sulphuric acid and sulphurous acid.

In case where the phenol protection group forms with the rest of the molecule an acetal, the substituent $R^{2'}$ is preferably

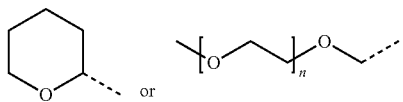

with n=0 or 1.

Hence, the acetals formed so are preferably methoxymethyl ether (MOM-ether), 1-methoxyethoxymethyl ether (MEM-ether) or tetrahydropyranyl ether (THP-ether). The protection group can easily be removed by acid.

The protecting group is introduced by reaction of the compound of formula (V) or (V') with a protecting agent.

The protecting agents leading to the corresponding phenol protection groups are known to the person skilled in the art, as well as the chemical process and conditions for this reaction. If, for example, the phenol protection group forms with the rest of the molecule an ester, the suitable protecting agent is for example an acid, an anhydride or an acyl halide.

In the case that an ester is formed by the above reaction with the protecting agent, and that said ester is an ester of an organic polycarboxylic acid or an inorganic polyprotic acid, not necessarily all acid groups are esterified to qualify as protected in the sense of this document. Preferable esters of inorganic polyprotic acids are phosphates.

It is preferred that the protection group $R^{2'}$ is a benzoyl group or a $C_{1-4}$-acyl group, particularly acetyl group or trifluoroacetyl. The molecules in which $R^{2'}$ represents an acyl group, particularly an acetyl group, can be easily prepared from the corresponding unprotected molecule by esterification, respectively the phenolic compound can be obtained from the corresponding ester by ester hydrolysis.

The phenol protecting group is preferably selected such that it is cleaved inside the human or animal body, particularly in the stomach.

As compound of formulae (III), (III') and (III-A) are important intermediates in the preparation of compound of formula (I) or (V) or (V'), respectively, as described above in detail, further aspects of the present invention are compound of formula (III') or of formula (III-A), respectively.

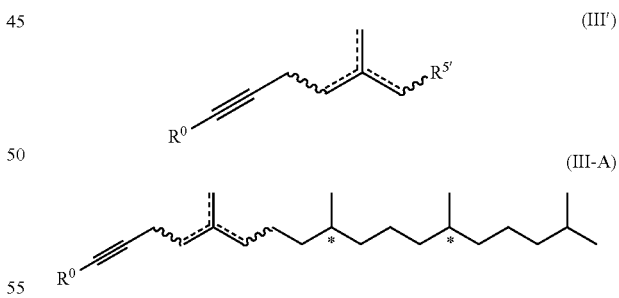

wherein * represents a chiral centre;
$R^0$ represents either H or $SiR'_3$ wherein R' represents independently from each other a linear or branched $C_{2-8}$-alkyl group or a $C_{6-12}$-aryl group;
$R^{5'}$ represents a completely saturated $C_{5-25}$-alkyl group; and wherein the dotted line indicates a double bond which is localized in one of the three indicated positions;
and wherein the wavy line represents a carbon-carbon bond which when linked to the carbon-carbon double bond is either in the Z or in the E-configuration.

Particularly, R⁰ represents Si(CH₃)₃ or Si(CH(CH₃)₂)₃ (=Si(iPr)₃ or Si(C₆H₅)₃ (=Si(ph)₃) or SiCH₃(C₆H₅)₂ or Si(CH₃)₂C₆H₅.

Particularly, R⁰ is Si(CH₃)₃ or Si(CH₂CH₃)₃(=SiEt₃) or Si(CH(CH₃)₂)₃(=Si(iPr)₃) or Si(C₆H₅)₃ (=Si(ph)₃) or SiCH₃(C₆H₅)₂ or Si(CH₃)₂C₆H₅ or Si(CH₃)₂(C(CH₃)₃).

It is preferred that R⁰ represents H.

In a further embodiment the invention relates to specific compounds compounds of above mentioned formula (III)

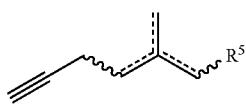

(III)

wherein R⁵ is of formula (IV)

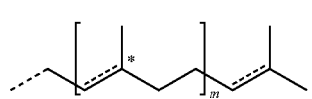

(IV)

with the proviso that at least one of said double bonds having dotted lines ( - - - - - - ) represents a single carbon-carbon bond.

Particularly such compounds are selected from the group consisting of 5,9,13,17-tetramethyloctadeca-4,16-dien-1-yne, 5,9,13,17-tetramethyloctadeca-4,12,16-trien-1-yne, 5,9,13,17-tetramethyloctadeca-4,8,16-trien-1-yne, 5,9,13,17-tetramethyloctadeca-4,12-dien-1-yne, 5,9,13,17-tetramethyloctadeca-4,8,12-trien-1-yne, 5,9,13,17-tetramethyloctadeca-4,8-dien-1-yne, 5,9,13,17-tetramethylocta-deca-4,8,16-trien-1-yne and 5,9,13,17-tetramethyloctadeca-4,8,12-trien-1-yne.

More particularly, such specific compound of formula (III) are selected from the group consisting of (E)-5,9,13,17-tetramethyloctadeca-4,16-dien-1-yne, (4E,12E)-5,9,13,17-tetramethyloctadeca-4,12,16-trien-1-yne, (4E,8E)-5,9,13,17-tetramethyloctadeca-4,8,16-trien-1-yne, (4E,12E)-5,9,13,17-tetramethyloctadeca-4,12-dien-1-yne, (4E,8E,12E)-5,9,13,17-tetramethyloctadeca-4,8,12-trien-1-yne, (4E,8E)-5,9,13,17-tetramethyloctadeca-4,8-dien-1-yne, (4E,8E)-5,9,13,17-tetramethyloctadeca-4,8,16-trien-1-yne and (4E,8E,12E)-5,9,13,17-tetramethyloctadeca-4,8,12-trien-1-yne.

EXAMPLES

General

The solvents were purchased from Fluka. All solvents and other chemicals were used without further purification. All reactions were carried out under argon. The reactions were monitored using GC. The crude products were analyzed by GC (area %), HPLC with external standard and quantitative NMR.

Gas Chromatography

The GC analyses have been performed on an Agilent HP-6850 series system. The separation is achieved on an HP-1 Methyl Siloxane (30 m×0.32 mm, 0.25 m) column with the following temperature program 50° C. (0 min)→10°/min→300° C. (5 min). The samples were dissolved in ethyl acetate (5 mg in 1 mL) and 1 μL was injected with a split ratio of 50:1.

GC-MS

GC-MS analysis was carried out on a Hewlett-Packard HP-6890, MSD-5973 series system. The separation is achieved on an HP-5MS (30 m×250 m, 0.25 m) column with the following temperature program:

70° C.(0 min)→(10° C./min)→315° C.(15 min).

The mass spectra have been generated by electron ionization.

IR

IR spectra have been generated on a Perkin Elmer Spectrum One FT-IR spectrometer in the range of 4000-600 cm⁻¹ with a resolution of 4 cm⁻¹ using 16 accumulations.

NMR

The NMR spectra were recorded on a Bruker Avance 300 spectrometer equipped with a 5 mm BBO BB-1H probe head operating at 300 MHz for ¹H and 75.5 MHz for ¹³C. Spectra were recorded in CDCl₃ and were referenced to residual chloroform (7.26 ppm CHCl₃; 77.0 ppm CHCl₃).

Synthesis of (4-bromobut-1-yn-1-yl)triisopropylsilane

Equipment: 200-mL 4-necked flask, solid CO₂ (−75° C.), Icebath (0° C.), 50 mL dropping funnel, argon bubbler, thermometer, magnetic stirring bar.

The equipment was carefully dried and flushed with argon. Under argon 2.0 g 4-bromobut-1-yne (14.6 mmol) was dissolved in 45 mL dry THF. The solution was cooled to −75° C. using solid CO₂. N-Butyl lithium in hexane was added dropwise (10.9 mL of 1.6 M solution in hexane, corresponding to 17.5 mmol, 1.2 equiv) over five minutes. The temperature of the solution rose to −30° C. The mixture was stirred for 15 minutes. Then 3.2 g chlorotriisopropylsilane (16.1 mmol, 1.1 equiv.) in 6 mL dry THF was added drop-wise. The mixture was allowed to warm to 0° C. The conversion was monitored by TLC (heptane/methyl-tert.-Butylether (MTBE)=20/1 v/v). After 1 h the silylation reaction was complete and the reaction mixture was carefully quenched with 50 mL 10% aqueous NH₄Cl solution. The aqueous phase showed pH 4. The organic layer was washed twice with 50 mL each desalted water. The aqueous layer was extracted twice with 50 mL each diethyl ether. The combined organic phases were dried over Na₂SO₄, filtered and concentrated at 20° C. bath temperature and 15 mbar during 1 h.

4.02 g of crude (4-bromobut-1-yn-1-yl)triisopropylsilane were obtained as a yellow oil with a purity of 86% (GC-MS). Characterization:

¹H NMR (300 MHz, CDCl₃) δ=3.45 (t, J=7.3 Hz, 2H), 2.81 (t, J=7.3 Hz, 2H), 1.12-1.00 (m, 21H).

¹³C NMR (75 MHz, CDCl₃) δ=104.87, 83.08, 29.73, 24.37, 18.59, 11.22.

Synthesis of the bromotriphenl(4-(triisopropylsilyl) but-3-yn-1-yl)phosphorane

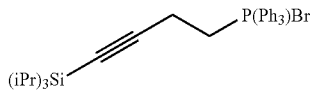

Equipment: 100 ml 4-necked round bottom flask, septum, reflux condenser, syringe pump, magnetic stirring bar, argon supply.

The glassware was dried under argon using a heat gun, then cooled to 23° C. under vacuum and flushed with argon. The flask was then charged with 12.23 g triphenylphosphane (46.6 mmol) and diluted in 25 mL toluene leading to a colourless solution. Using a syringe pump 16.58 g (4-bromobut-1-yn-1-yl)triisopropylsilane (42.4 mmol) were added over two hours. The addition was slightly exothermic, the colour of the solution turned to yellow. The solution was then heated with an oil-bath (135° C.) to reflux overnight. After 15 hours the phosphonium salt had precipitated. The reaction mixture was allowed to cool to 23° C. The suspension was then filtered over a G3 filter. Toluene was replaced with n-pentane. The remainder was rinsed with pentane. After drying at 40° C. and 20 mbar, 20.13 g crude bromotriphenyl(4-(triisopropylsilyl)but-3-yn-1-yl)phosphorane (white crystals) was obtained in a purity of 77% (yield 66%).

Synthesis of triisopropyl(5,9,13,17-tetramethyloctadec-4-en-1-yn-1-yl)silane

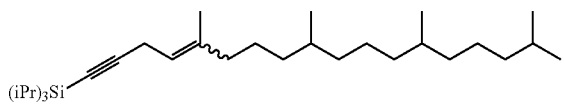

Equipment: 350 ml 4-necked round bottom flask, 25 ml dropping funnel, magnetic stirring bar, argon supply, thermometer, ice-bath The glassware was dried as described above. The flask was then charged with 20 g bromotriphenyl-(4-(triisopropylsilyl)but-3-yn-1-yl)phosphorane (27.9 mmol) and 200 mL dry THF leading to a white suspension. The suspension was cooled to 5° C.

n-Butyl lithium in hexane (17.45 mL, 1.6 molar, 27.9 mmol) was added using a dropping funnel over a period of 35 minutes. The solution turned immediately to orange and finally to dark red at the end of the addition. The solution was stirred for five minutes.

6,10,14-trimethylpentadecan-2-one (7.50 g, 27.9 mmol) was added over five minutes. The inner temperature rose to 11° C. Stirring was continued for 4 h at 5° C. Finally the reddish-brown suspension was allowed to warm to RT and then stirred for another 1 h. The reaction mixture was then quenched with 250 mL ice-water. The aqueous layer was subsequently extracted with three times each 250 mL heptane and the combined organic layers were washed with 250 mL aqueous 10% NaCl-solution. The organic layer was dried over $Na_2SO_4$, filtered and concentrated at 40° C. and 20 mbar. The crude product was obtained in 20.61 g as a mixture of brown oil and white crystals. This mixture was then suspended in 200 mL n-hexane, cooled overnight in a freezer to −20° C. The white crystals were filtered over a G3 filter, the filtrate was concentrated at 40° C. and 20 mbar.

The crude triisopropyl(5,9,13,17-tetramethyloctadec-4-en-1-yn-1-yl)silane was obtained in 20.06 g as brown oil in a purity of 47% (yield 76%).
Characterization:
$^1$H NMR (300 MHz): δ=0.83 (s, 3H, $CH_3$); 0.86 (s, 6H, $CH_3$); 0.88 (s, 3H, $CH_3$); 1.05 (s, 18H, TIPS-$CH_3$) 1.07 (s, 3H, $CH_3$); 1.08 (s, 3H, CH—Si); 0.99-1.15 (m, 16H, $CH_2$); 1.20-1.41 (m, 3H, CH); 1.69 (d, 2H, J=1.3 Hz, CH); 2.95 (dd, 2H, J=6.8, 1.1 Hz, $CH_2$); 5.20 (t, J=6.78 Hz, 1H, CH).

$^{13}$C NMR (75 MHz) δ in ppm: δ=11.3; 11.4; 18.5; 18.7; 18.8; 22.7; 22.74; 24.5; 24.8; 28.0; 32.8; 32.81; 37.3; 37.4; 39.4; 39.7; 79.4; 107.9; 118.9; 119.5; 137.7.

Synthesis of 5,9,13,17-tetramethyloctadec-4-en-1-yne

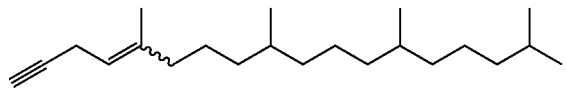 [SMILES: C#CCC=C(C)CCCC(C)CCCC(C)CCCC(C)C]

Equipment: 250 ml round-bottom flask, magnetic stirrer, dropping funnel.

The flask was charged with 9.9 g triisopropyl(5,9,13,17-tetramethyloctadec-4-en-1-yn-1-yl)silane (21.5 mmol), 100 mL THF and 0.8 mL desalted water leading to a colourless solution. Cooling the solution to 2° C. During 25 minutes a solution of 9.2 g tetrabutylammonium fluoride hydrate in 36 mL THF was added. The mixture was stirred overnight. The reaction mixture was quenched with 200 mL 10% $NaHCO_3$ and the aqueous phase extracted three times with 200 mL MTBE each. The combined organic layers were washed with 200 mL aqueous 10% NaCl. The combined organic layers were dried over $Na_2SO_4$, filtered and dried at 40° C. and 20 mbar.

The crude product was obtained in 9.72 g as light brown oil in a purity of 60% (GC-MS total ion count). The product was purified by column chromatography using pentane as eluent furnishing 4.31 g 5,9,13,17-tetramethyloctadec-4-en-1-yne (61% yield, purity of 93% q-NMR).
Characterization:
$^1$H NMR (300 MHz): δ=0.84 (d, 3H, J=2.3 Hz, $CH_3$), 0.85-0.87 (m, 6H), 0.88 (s, 3H, $CH_3$), 1.04-1.42 (m, 18H, CH, $CH_2$), 1.48-1.55 (m, 1H, $CH_2$), 1.62 (s, 1H, $CH_2$), 1.71 (d, 2H, J=1.1 Hz, M05), 1.91-2.05 (m, 2H, $CH_2$), 2.85-2.94 (m, 2H, $CH_2$), 5.16-5.24 (m, 1H, CH).

$^{13}$C NMR ($CDCl_3$, 75 MHz): δ=138.5, 138.3 (E+Z), 118.6, 118.0 (E+Z), 83.6, 67.6, 67.6, 39.7, 39.4, 37.4, 37.3, 37.0, 36.9, 36.8, 36.7, 32.8, 32.7, 32.7, 32.1, 28.0, 25.2, 24.8, 24.5, 23.3, 22.8, 22.7, 19.8, 19.7, 19.7, 17.5, 17.4, 16.0 ppm.
GC-MS: M+454.4; 411.3; 205.1; 157.1; 135.0; 109.1; 69.0; 41.0.
IR ($cm^{-1}$): 3314, 2952; 2925; 2120; 1667.

Synthesis of 3,6-dimethyl-2-(3,7,11,15-tetramethyl-hexadec-2-en-1-yl)phenol

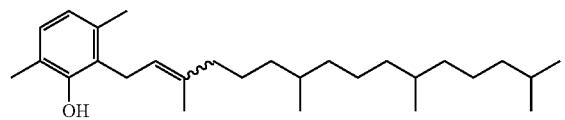 [SMILES: CC(=CCc1c(C)ccc(C)c1O)CCCC(C)CCCC(C)CCCC(C)C]

Equipment: Glovebox, 10 ml vial, magnetic stirring bar, heating device.

In the vial are placed 0.027 g $AgSbF_6$ (0.08 mmol), 0.047 g CyJohnPhosAuCl (0.08 mmol), 0.429 mL 2,5-dimethylfuran (4 mmol) and 1.218 g 5,9,13,17-tetramethyloctadec-4-en-1-yne (4 mmol). Dichloromethane (4 mL) is added leading to a dark purple mixture. The mixture was stirred for 94 h at 60° C.

The suspension were filtered over celite, the filter washed with $CH_2Cl_2$.

The filtrate was concentrated at 40° C. giving 1.6 g brownish dark oil. The purification was achieved with column chromatography (pentane/MTBE) leading to 0.69 g of the desired 3,6-dimethyl-2-(3,7,11,15-tetramethylhexadec-2-en-1-yl)phenol (sum of all 8 stereoisomers, 20% yield).

Characterization:

$^1$H NMR (CDCl$_3$, 300 MHz): δ=6.88 (d, J=7.3 Hz, 1H), 6.66 (d, J=7.5 Hz, 1H), 5.33+5.16 (2t, J=6.78 Hz, J=7.16 Hz, E+Z 1H), 5.11 (d, J=3.8 Hz, 1H), 3.37+3.12 (2d, J=7.16+ 6.78 Hz, E+Z, 2H), 2.27 (s, 3H), 2.14 (s, 3H), 1.99 (t, J=7.5 Hz, 2H), 1.74+1.73 (2t, J=4.14 Hz, E+Z, 2H), 1.48-1.57 (m, 4H), 1.03-1.41 (m, 16H), 0.88 (d, J=6.22 Hz, 6H), 0.86 (d, J=6.22 Hz, 6H).

$^{13}$C NMR (75 MHz, CDCl$_3$) δ=139.99+138.91 (E+Z), 128.12, 122.01, 121.9; 116.11, 43.23, 39.41, 37.42, 37.33, 36.95, 32.82, 32.75, 32.34, 29.47, 28.01, 25.75, 25.24, 24.84, 24.49, 23.46, 22.75, 22.65, 19.90, 19.78, 19.71, 15.83. IR (cm$^{-1}$): 3481; 2951, 2924, 2866, 1582, 1492, 1462.

HRMS: found M=400.3693, $C_{28}H_{28}O$. Calc. 400.37.

Synthesis of 2,5-dimethyl-3-(3,7,11,15-tetramethyl-hexadec-2-en-1-yl)quinone

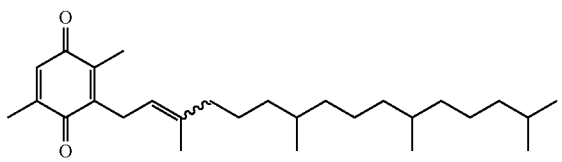 [SMILES: CC(=CCC1=C(C)C(=O)C=C(C)C1=O)CCCC(C)CCCC(C)CCCC(C)C]

Equipment: 10 ml 2-necked-round bottom flask, magnetic stirring bar, thermometer The starting material 3,6-dimethyl-2-(3,7,11,15-tetramethylhexadec-2-en-1-yl)phenol (0.2 g, 0.299 mmol) was dissolved in ethanol (3 mL) and the the solution cooled to 10° C. The catalyst salcomine (19.6 mg, 0.12 mmol, 0.24 eq.) and another 3 mL ethanol was added. An air stream was flowing over the solution for 20 hours at 23° C. leading to a dark-brown reaction mixture.

The solvent was evaporated at 40° C. and 20 mbar, leading to 0.14 g of brown oil that contained some small dark particles. For purification the crude product was diluted in pentane and chromatographed (eluent 100% pentane). The 2,5-dimethyl-3-(3,7,11,15-tetramethylhexadec-2-en-1-yl)quinone was obtained in 33 mg as yellow oil.

Characterization:

$^1$H NMR (CDCl$_3$, 300 MHz): δ=6.55 (d, J=1.5 Hz, 1H); 4.94 (2t, J=6.9, 8.1; E+Z, 1H); 3.21 (d, J=7 Hz, 2H); 2.04 (d, J=1.5 Hz, 3H); 2.02 (s, 3H); 2.0-1.84 (m, 3H); 1.71-1.75 (m; 2H); 1.65-1.68 (m, 2H); 1.46-1.55 (m, 4H); 1.4-1.0 (m); 0.88 (d, J=6.6 Hz, 6H); 0.85 (d, J=8.1 Hz, 6H).

$^{13}$C NMR (75 MHz, CDCl$_3$) δ=145.37, 140.58, 138.21, 133.03, 119.45, 40.04, 39.41, 37.42, 37.33, 37.16, 37.07, 32.81, 32.31, 29.73, 28.01, 25.42, 24.84, 24.50, 23.42, 22.75, 22.66, 19.72, 16.25, 15.96, 11.92.

Synthesis of 2,5-dimethyl-3-(3,7,11,15-tetramethyl-hexadec-2-en-1-yl)hydroquinone

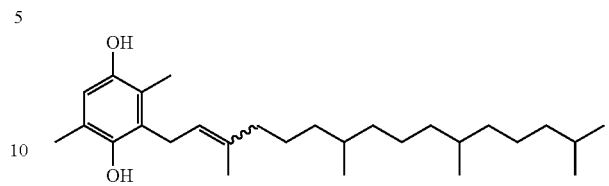

Equipment: 10 ml 2-necked-round bottom flask, magnetic stirring bar, septum, syringe, light shield.

Under argon atmosphere the starting material 2,5-dimethyl-3-(3,7,11,15-tetramethylhexadec-2-en-1-yl)hydroquinone (0.033 g, 0.08 mmol) was taken up in THF (0.4 mL) and shielded from light under a black towel. Into the resulting yellow solution was added a solution of sodium dithionate (0.039 g) in water (0.2 mL) over 30 minutes (dropwise addition via syringe). The reaction mixture was stirred for 30 min. and afterwards the THF was removed. According to TLC the reaction was still not complete. Another solution of sodium dithionate (0.039 g in 0.2 mL water) was added and stirred overnight. For work-up the reaction was extracted three times with 1 mL each dichloromethane. The combined organic phases were washed three times with 1 mL each water. The organic phase was dried over sodium sulfate, filtered and concentrated under reduced pressure (40° C., 10 mbar). The 2,5-dimethyl-3-(3,7,11,15-tetramethylhexadec-2-en-1-yl)hydroquinone was obtained in 27 mg as a light yellow solid. It was immediately transformed in the following reaction step.

Synthesis of β-tocopherol

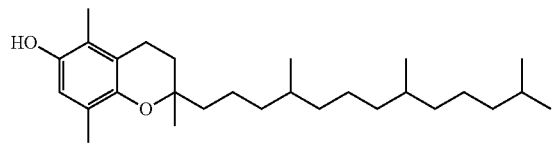 [SMILES: Cc1cc(O)c(C)c2c1OC(C)(CCCC(C)CCCC(C)CCCC(C)C)CC2]

Equipment: 10 ml round-bottom flask, magnetic stirring bar, reflux condenser, argon supply.

Under argon at 23° C. the flask was charged with 27 mg 2,5-dimethyl-3-(3,7,11,15-tetramethylhexadec-2-en-1-yl) hydroquinone (0.065 mmol), 1 mL ethylene carbonate, and 1 mL n-heptane leading to a light yellow biphasic mixture. Under vigorous stirring one drop of sulfuric acid was added. The mixture was heated to 120° C. and refluxed for three hours.

After three hours, the reaction mixture was cooled to room temperature. Three phases were obtained, one solid phase and two liquid phases. The reaction mixture was diluted with heptane (4 mL). The layers were separated and the ethylene carbonate layer was washed with 4 mL heptane. The combined heptane layers were concentrated under reduced pressure at 20 mbar giving 29 mg of a brown oil. The crude product was analyzed by NMR, GC-MS and LC-MS. The spectra and chromatograms were shown to be identical to analyses of commercially available β-tocopherol.

The invention claimed is:
1. A process of preparing a compound of formula (I):

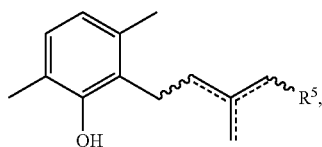

wherein
the process comprises the step of reacting in a reaction mixture a compound of formula (II):

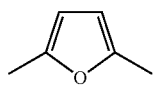

with a compound of formula (III):

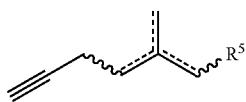

in the presence of a gold(I) complex, wherein
$R^5$ represents either a completely saturated $C_{5-25}$-alkyl group or a $C_{5-25}$-alkyl group comprising at least one carbon-carbon double bond; and wherein
the dotted line indicates a double bond which is localized in one of the three indicated positions; and wherein
the wavy line represents a carbon-carbon bond which when linked to the carbon-carbon double bond is either in the Z or in the E-configuration.

2. The process according to claim 1, wherein that the gold(I) complex has the formula [Au(I)OL]AN, wherein OL represents an organic ligand and AN represents a single charged anion.

3. The process according to claim 1, wherein the gold(I) complex has a single charged anion (AN) which is selected from the group consisting of $[BX_4]^-$, $[PX_6]^-$, $[SbF_6]^-$, $[ClO_4]^-$, $CF_3COO^-$, a sulfonate of formula (AN-II), tetra(3,5-bis(trifluoromethyl)phenyl)borate $(BAr_F^-)$, tetraphenylborate, and anions of formula (AN-I):

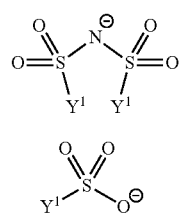

wherein X represents a halogen atom; and
$Y^1$ represents a phenyl or a $C_{1-8}$-alkyl group which may be substituted by at least one halogen atom.

4. The process according to claim 1, wherein the gold(I) complex has an organic ligand (OL) which is either:

(i) at least one phosphorous containing ligand which is selected from the group consisting of formula (P1), (P2), (P3), (P4), (P5), (P6), (P7) and (P8);
or
(ii) an imidazole-2-ylidene ligand which is a compound of formula (IM));
or
(iii) at least one 1H-1,2,3-triazol ligand selected from the group consisting of the ligands of formulas (TR-1), (TR-2) and (TR-3);

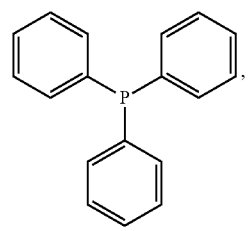

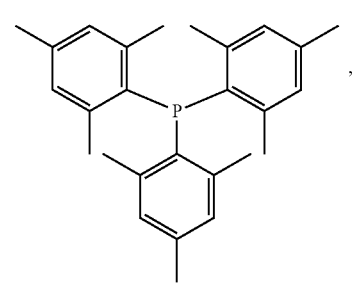

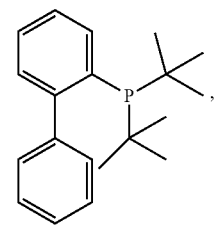

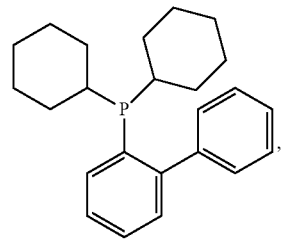

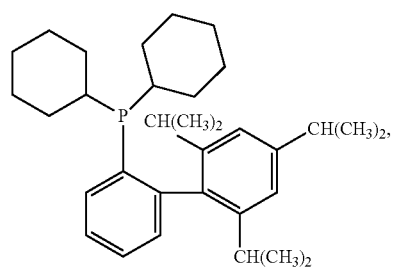

-continued

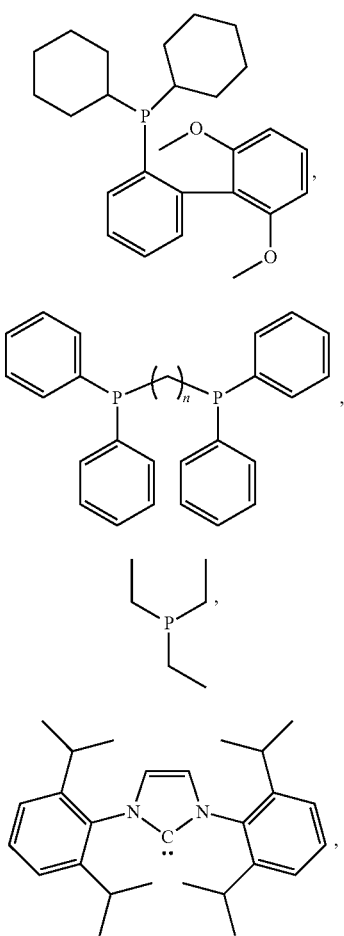

(P6)

(P7)

(P8)

(IM)

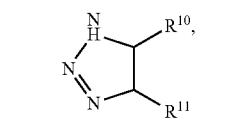

(TR-1)

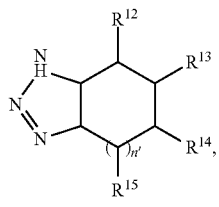

(TR-2)

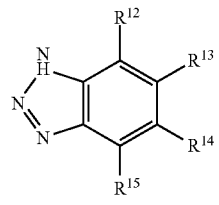

(TR-3)

wherein $R^{10}$ and $R^{11}$ represent independently from each other either H or a linear or branched $C_{1-10}$-alkyl or $C_{4-10}$-cycloalkyl group; and wherein $R^{12}$, $R^{13}$, $R^{14}$ and $R^{15}$ represent independently from each other H or a linear or branched $C_{1-6}$-alkyl group;

n stands for an integer of 1-6 and n' is 0, 1 or 2.

5. The process according to claim 1, which comprises preparing the gold(I) complex by reacting a gold(I) chloro complex and a silver(I) salt.

6. The process according to claim 5, wherein the gold (I) complex is of formula [Au(I)OL]AN, wherein OL represents an organic ligand and AN represents a single charged anion, and wherein the gold (I) complex is prepared by the reaction of Au(I)OLCl and AgAN.

7. The process according to claim 1, wherein $R^5$ is of formula (IV):

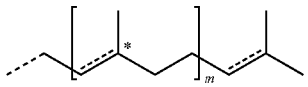
(IV)

wherein m represents an integer being 0, 1, 2, 3 or 4; and wherein the dotted line represents the bond by which the substituent of formula (IV) is bound to the rest of the compound of formula (I) or formula (III); and wherein the double bonds having dotted lines

represent independently from each other either a single carbon-carbon bond or a double carbon-carbon bond; and wherein the symbol * indicates a chiral centre in case the respective double bond having dotted line

represents a single carbon-carbon bond.

8. The process according to claim 1, wherein the process comprises forming the gold(I) complex in situ in the reaction mixture.

9. The process according to claim 1, wherein the gold(I) complex is present in the reaction mixture in a molar ratio of the gold(I) complex to the compound of formula (II) of 1:2 to 1:10,000.

10. The process according to claim 1, wherein the compound of formula (III) is a compound prepared from a compound of formula (XIII-a) and from a compound of formula (XIII-b)

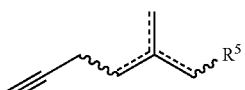
(III)

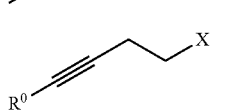
(XIII-a)

(XIII-b)

wherein X represents a halogen atom, and wherein $R^0$ represents either H or $SiR'_3$, wherein R' represents independently from each other a linear or branched $C_{2-8}$-alkyl group or a $C_{6-12}$-aryl group.

11. The process according to claim 1, wherein the compound of formula (III) is prepared from compound of formula (III-aa) in the presence of fluoride ions:

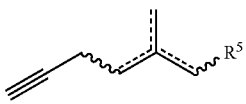

(III)

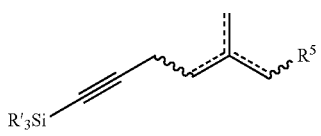

(III-aa)

wherein R' represents independently from each other a linear or branched $C_{2-8}$-alkyl group or a $C_{6-12}$-aryl group.

12. A compound of formula (III'):

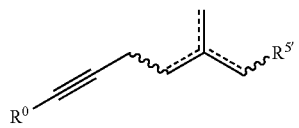

(III')

wherein $R^0$ represents either H or $SiR'_3$ wherein R' represents independently from each other a linear or branched $C_{2-8}$-alkyl group or a $C_{6-12}$-aryl group; and $R^{5'}$ represents a completely saturated $C_{5-25}$-alkyl group; and wherein the dotted line indicates a double bond which is localized in one of the three indicated positions; and wherein the wavy line represents a carbon-carbon bond which when linked to the carbon-carbon double bond is either in the Z or in the E-configuration.

13. A compound of formula (III-A):

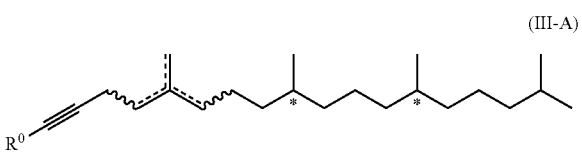

(III-A)

wherein the symbol * represents a chiral centre;

$R^0$ represents either H or $SiR'_3$, wherein R' represents independently from each other a linear or branched $C_{2-8}$-alkyl group or a $C_{6-12}$-aryl group; and wherein the dotted line indicates a double bond which is localized in one of the three indicated positions; and wherein the wavy line represents a carbon-carbon bond which when linked to the carbon-carbon double bond is either in the Z or in the E-configuration.

* * * * *